(12) United States Patent
Dieplinger

(10) Patent No.: US 7,767,406 B2
(45) Date of Patent: Aug. 3, 2010

(54) METHOD FOR DIAGNOSING TUMORS

(75) Inventor: Hans Dieplinger, Innsbruck (AT)

(73) Assignee: Vitateq Biotechnology GmbH, Innsbruck (AT)

( * ) Notice: Subject to any disclaimer, the term of this patent is extended or adjusted under 35 U.S.C. 154(b) by 74 days.

(21) Appl. No.: 11/814,905

(22) PCT Filed: Jan. 31, 2006

(86) PCT No.: PCT/AT2006/000036

§ 371 (c)(1), (2), (4) Date: Jul. 26, 2007

(87) PCT Pub. No.: WO2006/079136

PCT Pub. Date: Aug. 3, 2006

(65) Prior Publication Data

US 2008/0166737 A1    Jul. 10, 2008

(30) Foreign Application Priority Data

Jan. 31, 2005    (AT) ............................... A 149/2005

(51) Int. Cl.
G01N 33/53  (2006.01)
(52) U.S. Cl. ..................... 435/7.1; 435/7.23; 530/387.1
(58) Field of Classification Search ................... 435/7.1, 435/7.23; 530/387.1
See application file for complete search history.

(56) References Cited

U.S. PATENT DOCUMENTS

| 5,652,352 A | 7/1997 | Lichenstein et al. ......... 536/23.5 |
| 2002/0055182 A1 | 5/2002 | Illmensee et al. ........... 436/510 |
| 2004/0235718 A1 | 11/2004 | Becker-Andre et al. ....... 514/12 |

FOREIGN PATENT DOCUMENTS

| WO | WO 95/027059 | 10/1995 |
| WO | WO 01/01148 | 1/2001 |
| WO | WO 02/50549 | 6/2002 |
| WO | WO 2005/034732 | 4/2005 |
| WO | WO 2006/079136 | 8/2006 |

OTHER PUBLICATIONS

Woodtli et al, 1974, Virchows Arch A Path Anat Histol, 364,: 93-110.*
Korkola et al, 2005, Oncogene, 24: 5101-5107.*
Van de Geijn et al, 2009, Birth defects Res (part C), 87: 96-113.*
Kaiser, 2006, Science, 313: 1370.*
Eble et al, 1984, J Urology, 131: 546-550.*
Abbaszadegan, M R, et al, 1994, Cancer Res, 54: 4676-4679.*
Nogales et al, 1979, Cancer, 43(2): 539-43.*
Stanton, P et al, 1994, Br J Cancer, 70: 427-433.*
Iehle, C et al, 1999, J Steroid Biochem Mol Biol, 68: 189-195.*
Austrian Office Action, Austrian Application No. A 149/2005, Sep. 7, 2005.
Charokopos et al., "Increased levels of albumin in bronchial washing fluid of patients with bronchial carcinoma. Could albumin be considered as a tumor marker?" 19(4):316-321, 2004.
Gadducci et al., "Serum tumor markers in the management of ovarian, endometrial and cervical cancer," *Biomed. Pharmacother.*, 58:24-38, 2004.
Hellerstedt et al., "Testicular cancer," *Curr. Opin. Oncol.*, 14:260-264, 2002.
Jerkovic et al., "Afamin is a novel human vitamin E-binding glycoprotein characterization and in vitro expression," *Journal of Proteome Research*, 4:889-899, 2005.
Lichenstein et al., "Afamin is a new member of the albumin, α-fetoprotein, and vitamin D-binding protein gene family," *The Journal of Biological Chemistry*, 269(27):18149-18154, 1994.
Mandelblatt et al., "Benefits and costs of using HPV testing to screen for cervical cancer ," *JAMA*, 287:2372-2381, 2002.
Parker et al., "Cancer statistics, 1996," *CA Cancer J. Clin.*, 46:5-27, 1996.
Sasieni, "Human papillomavirus screening and cervical cancer prevention," *J. Am. Med. Wom. Assoc.*, 55:216-219, 2000.
Sigounas et al., "dl-alpha-tocopherol induces apoptosis in erythroleukemia, prostate, and breast cancer cells," *Nutr. Cancer*, 28:30-35, 1997.
Voegele et al., "Characterization of the vitamin E-binding properties of human plasma afamin," *Biochemistry*, 41:14532-14538, 2002.
Whitehouse and Solomon, "Current status of the molecular characterization of the ovarian cancer antigen CA125 and implications for its use in clinical screening," *Gynecol. Oncol.*, 88:S152-7, 2003.
WHO: Human papillomavirus infection and cervical cancer, 2004, from.

* cited by examiner

*Primary Examiner*—Larry R. Helms
*Assistant Examiner*—Minh-Tam Davis
(74) *Attorney, Agent, or Firm*—Fulbright & Jaworski LLP

(57) ABSTRACT

The present invention describes a method for diagnosing tumours of the reproductive organs which is characterised by determination of the afamin content in a sample of a body fluid or in a tissue sample, wherein a tumour is diagnosed if the afamin content in the sample is decreased compared to the afamin content in a sample from a person without a tumour of the reproductive organs.

21 Claims, 13 Drawing Sheets

METHOD FOR DIAGNOSING TUMORS

This application is a national phase application under 35 U.S.C. §371 of International Application No. PCT/AT2006/000036 filed 31 Jan. 2006, which claims priority to Austrian Patent Application No. A 149/2005 filed 31 Jan. 2005. The entire text of each of the above-referenced disclosures is specifically incorporated herein by reference without disclaimer.

The present invention relates to a method for diagnosing tumours of the reproductive organs.

Tumours in the reproductive organs, in particular ovarian and testicular tumours, specifically affect young people (also a large group of people between 30 and 50). In most of these tumours, early diagnosis is paramount for survival. The reproductive system includes the gonads—male testes and female ovaries and other accessory ducts and glands (gonos=seed). These provide the means for reproduction, the continuation of the species, and passing on of genetic material to the next generation.

Ovarian tumours are blastomas of the ovary. Every third ovarian tumour is or develops into a carcinoma. Ovarian cancer is the 5th most common cancer in women and accounts for 5% of all cancers and 6% of all cancer deaths in females. 1 in 55 women will develop ovarian cancer sometime in their life. It is a major problem in routine medicine, because the symptoms of ovarian cancer are similar to those of non-cancerous cysts or tumours. Ovarian tumors are usually diagnosed by bimanual examination, ultrasonic examination, computer-tomography, laparoscopy and exploratory laparotomy.

The best-known and well-described serum marker of ovarian cancer is the CA125 antigen (Whitehouse et al. Gynecol Oncol 88, S152, 2003). Since the CA125 antigen is not only expressed on ovarian tumor cells but also by a number of different cell types, it does not have sufficient specificity and sensitivity to detect early ovarian cancer when used alone. Improvements in early diagnosis and reduced false-positive results maybe achieved if CA125 serum level is used in combination with other markers.

Testicular Cancer (TC) accounts for about 1% of neoplasms in men and can affect males from infancy to senility. TC is the most common malignancy in males between the ages of 15 and 35, the second most common cancer in men aging from 35 to 39 years, and the third most common malignancy in males aging from 15 to 19. The incidence TC is currently rising with approximately 7,000 new cases per year. In a study between 1988 and 1996 of active duty service members a 78% increase in TC has been observed during this nine year period.

Testicular neoplasms are classified into two major histological groups: germ cell tumours (95% of all testicular tumours) and nongerm cell tumours (4% to 5%). Germ cell tumours are divided into seminomas (S) which represent about 40% of all germ cell tumours, and nonseminomas (NS) which stand for up to 60% of all germ cell tumours. Nonseminomas are further divided into four categories: embryonal (15% to 20%), teratoma (20% to 25%), yolk sac (10%), and choriocarcinoma (1%)(for recent reviews, see Mac-Vicar et al., 2004 Curr Opin Oncol 16:253-256; Parker et al., 1996 CA Cancer J Clin 46:5-27; and Hellerstedt et al., Curr.Opin.Oncol.14 (2002), 260-264). Seminomas typically spread via regional lymph nodes to supraclavicular, mediastinal, and retroperitoneal nodes. Nonseminomas metastasize preferably to the liver and lungs by lymphatic and hematogeneous routes. While the survival rate for TC generally is generally good, survivability and curability of TC is extremely dependent upon early detection (Parker et al, 1996). Once the cancer has spread beyond the local nodes (Stage III) the survival rate drops dramatically, whereas the five-year survival rate for Stages I and II testicular cancer is better than 95%. In consequence, diagnosis at an earlier stage comes along with a better long-term prognosis, whereas delayed diagnosis is associated with increased patient mortality. This is, because of the lower response rate from the established treatment if tumour development is progressed.

As not every abnormal finding related to the testicle is a testicular neoplasm, great efforts should be made to separate between tumours and other disorders of the testicle such as epididymitis. As fine-needle biopsy, a commonly employed method for the confirmation of cancer diagnosis is contraindicated in the case a TC because of an increased risk of metastatic spread, radical surgical removal of the affected testicle is not only the first step in most treatment regimens but also often performed for definitive diagnosis.

Cervical cancer is the second most common cancer among women worldwide, with more than 500,000 new cases and about 288,000 death per year (WHO: Human papillomavirus infection and cervical cancer, 2004. Available on the World Wide Web at who.int/vaccine_research/diseases/hpv/enl). The situation is even worse in many developing countries where more than two thirds of the cervical cancers are diagnosed first at an advanced stage, which is typically combined with a very poor prognosis for survival. On the other hand, if precancerous lesions are identified in a timely manner and treatment is initiated immediately, deaths from cervical cancer would be completely preventable.

Cancer prevention programs are based on the finding that cervical cancer develops from mild (CIN I) to moderate (CIN II) and severe CIN (CIN III) and finally to cancer. Cervical intraepithelial neoplasia (CIN) describes precancerous changes of the cervix i.e. the abnormal growth of the epithelial tissue on the surface of the cervix. CIN progresses to cancer over a prolonged period of time (typically 5 to 20 years) and is asymptomatic. Thus, CIN can only be detected by suitable test procedures. While mild CIN may regress spontaneously, especially in young women, it is important to treat moderate or severe CIN because it may otherwise progress to cancer.

Several types of HPV (human papilloma virus), a commonly sexually transmitted infection, have been identified as the major causative agent for the development of precursor lesions. Some types of HPV, especially types 16 and 18, but also others like 31, 33, 35, 39, 45, 51, 52, 56, 58, 59, and 68 (commonly termed "high risk HPV") are associated with cervical intraepithelial neoplasia and are more likely to cause severe lesions and cancer. Although HPV infections are widespread in the population they can not be found in every cervical cancer patient. Furthermore, not all infections with high risk HPV result in cervical cancer. Therefore also other causative agents for the development of cervical cancer are postulated.

CIN usually occurs in the region of the cervix where the squamous epithelium of the ectocervix and the columnar epithelium of the endocervix meet. Cells from this zone must be sampled for cytological screening (i.e. Papanicolau screening) or need to be examined during visual screening procedures (i.e. colposcopy) the two most commonly used diagnostic tools besides HPV-DNA typing.

Papanicolaou screening makes use of the observation that CIN is a cellular change in which the ratio between the cell nucleus and the overall size of the cell is increased. The method was first described by Papanicolau in 1923, as method of collecting cells from the vaginal tract and smearing the cells on a glass slide for microscopic examination. Although still widely used, Papanicolaou screening is an only moderately effective screening technique. Recent meta-analysis studies have shown that Papanicolaou smear screening has an overall sensitivity of only about 50% for detection of any grade of CIN, which means that only half of the women with CIN are correctly diagnosed. The rate of false-negative Papanicolaou screening is estimated to be as high as 25% to 50% (Mandelblatt et al., JAMA 287 (2002), 2372-2381) because of poor sample collection, incorrect slide preparation, and laboratory interpretation errors. Interpretation of cytomorphological changes is highly subjective resulting in a high risk of misclassification. To obtain accurate Papanicolaou smear screening results, very well trained health care professionals are necessary to obtain cells from the transforming zone in the cervix. Furthermore, a well established cytology laboratory with experienced cytologists is another prerequisite to ensure not only the quality of sampling but also the accuracy of microscopical interpretation of the samples. All these limitations and sample to sample differences make it impossible to offer an effective Papanicolaou screening.

Although new technologies, such as thin-layer liquid-based cytology, have been developed to improve the accuracy of sampling, the interpretation of the cell morphology still remains the major source of misinterpretation and false diagnosis. In thin-layer liquid-based cytology, the sample is collected from the cervix mechanically by using a small brush (i.e. cytobrush) and suspended in a cell-preserving solution for automated slide preparation. The liquid is passed though a microfilter and the remaining cells are transferred as a monolayer from the microfilter to a slide. The slide itself is then processed and interpreted as a conventional Papanicoloau screening test, which generally limits the accuracy of this method. The sensitivity may be even lower when postmenopausal women are screened, because of changes in the cervix that make it difficult of obtaining adequate samples from the transformation zone. Furthermore, monolayer cytology (i.e. Thin-Prep, Cytyc Corporation, Boxborough, Mass.), which is apparently becoming widely used in the United States, is much more expensive than Papanicolaou screening. Epidemiological data suggest that current methods of Papaniclaou screening are unlikely to prevent more than 60% of cervical cancers in a population (Sasieni P. D., J Am Med Wom Assoc. 55 (2000), 216-219).

Visual screening (colposcopy)—another widely used method for cervical cancer detection—is the visual inspection of the cervix in order to find pathologic changes at the cervix transformation zone. In its beginning this approach used visual inspection alone and was very inaccurate in identifying precursor lesions. Visual inspection after previous "staining" of the cervix transformation zone with acetic acid has established this method as a simple and cost-effective screening technique. This modified visual inspection involves the insertion of a vaginal speculum and swabbing the cervix with 3% to 5% acetic acid solution prior to the visual inspection of the cervix. Normal epithelium appears in pink colour whereas CIN lesions will turn white for a few minutes after application of acetic acid because of the increased amount of nuclear proteins and cytokeratins in the cervical epithelium. Despite this improvement, the method remains limited in the accuracy of detecting CIN II and CIN III lesions. Furthermore, interpreting the results from colposcopy are, similar to Papanicolaou screening, highly dependent on the examiners experience.

Besides these, in the broader sense, visual-based screening procedures, HPV-DNA typing became more and more important during the last years. Recent advances in the detection of DNA from high-risk HPV (i.e. Hybrid Capture II test (Digene Corporation, Gaithersburg, Md.) in combination with the Polymerase Chain Reaction (PCR)), have enabled HPV testing to be used as a screening tool for HPV associated cervical intraepithelial neoplasia and cervix cancer. The Hybrid Capture II DNA assay uses non-radioactive ribonucleic acid probes in a modified enzyme-linked immunosorbent assay (ELISA) to detect DNA from high-risk HPV species. Although HPV testing is effective, its distribution is limited by the fact that it is more expensive than Papanicolaou screening. According to FDA guidelines, the HPV DNA test is not intended to replace regular Papanicolaou screening or to screen women under the age of 30 with normal Papanicolaou screening results. Furthermore, HPV-DNA testing is per se limited to HPV induced CIN lesions and HPV induced cervical cancers.

Staging of Cervical Cancer has been developed to describe the extent of cancer growth. The stage of cervical cancer describes the tumour's size, depth of penetration within the cervix and spread within and beyond the cervix. Cervical cancer staging is usually described in terms of the FIGO system, a staging scheme developed by the International Federation of Gynecology and Obstetrics. The FIGO classifications are grouped within basic stages labeled stage 0 through stage IV (0-4):

Stage 0 or carcinoma in situ is very early cancer. The abnormal cells are found only in the first layer of cells of the lining of the cervix and do not invade the deeper tissues of the cervix.

Stage I cancer involves the cervix but has not spread nearby.

Stage IA indicates a very small amount of cancer that is only visible under a microscope is found deeper in the tissues of the cervix.

Stage IB indicates a larger amount of cancer is found in the tissues of the cervix.

Stage II cancer has spread to nearby areas but is still inside the pelvic area.

Stage IIA cancer has spread beyond the cervix to the upper two-thirds of the vagina.

Stage IIB cancer has spread to the tissue around the cervix.

Stage III cancer has spread throughout the pelvic area. Cancer cells may have spread to the lower part of the vagina. The cells also may have spread to block the tubes that connect the kidneys to the bladder.

Stage IV cancer has spread to other parts of the body.

Stage IVA cancer has spread to the bladder or rectum (organs close to the cervix).

Stage IVB cancer has spread to other organs such as the lungs.

Despite the ability to reduce the incidence of cervical cancer significantly by early detection (especially prior to stage o (pre-stage 0)), there are still limitations currently in the screening process for this disease. Most dominant is the fact that many patients are not aware of the currently available screening methods. Detecting cervical cancer in serum samples within routineously performed serum analysis would solve this problem. Present screening procedures are not able to detect CIN and/or cervical cancer in serum samples, they are designed for the analysis of cervical cells. All the screening procedures established thus far have their specific limitations and none of these methods allows the detection of CIN or cervical cancer in samples other than derived from the transforming region of the cervix. Furthermore, each of these screening programs is far beyond the possibility to be used for a population screening especially in developing countries.

This situation would change dramatically with the development of precise, rapid, and inexpensive CIN and/or cervical cancer diagnostic tools.

Clearly, better diagnostic tools, with a higher specificity and a higher sensitivity are a matter of urgent necessity. With respect to this, serum markers would not only be helpful indicators of cancers of the reproductive system, especially TC, ovarian cancer and cervical cancer, but could also be used for diagnosis, staging, and follow up of these tumour forms.

Presently, for example, several serum markers are used to diagnose neoplasms of the testis:

(1) The β-subunit human chorionic gonadotropin (β-HCG) is elevated in 30% to 35% of nonseminomatous germ cell tumors and 10% to 25% in patients with seminoma. This is most likely due to the ability of some tumours to secrete abundant amounts β-HCG. (2) Alpha-fetoprotein (AFP) levels are known to be elevated in approximately 55% of cases of nonseminomatous germ cell tumours, but not in seminomas. (3) Lactate dehydrogenase (LDH) is elevated in about 50% of all patients with testicular neoplasms. LDH is usually elevated in proportion to tumour volume and not specific to any one tumour category. As LDH is expressed in several tissues, abnormal levels of LDH often reflect other disease entities. Despite the fact that HCG, AFP, and LDH levels should be deliberated in all patients before a radical surgical removal of the affected testicle (orchiectomy) is performed, the very limited predictive value of all three serum markers is obvious, because of the large group of patients that are negative for these classical markers. Thus, in most cases clinicians can not put the decision whether or not to perform an orchiectomy on these three diagnostic markers. Furthermore, also after orchiectomy the predictive value of HCG, AFP and LDH serum levels remain critical when monitoring treatment of the respective cancers. Thus, new tumour markers for testicular neoplasms are urgently needed either as stand alone markers, as well as markers to be combined with existing diagnostic tools. Unfortunately, LDH is expressed in several tissues and increased concentrations of LDH therefore often reflect other disease entities.

Several other new tumor markers (including epidermal growth factor, NES-1 and i(12p)) have been reported (Hellerstedt et al., 2002 Curr Opin Oncol 14:260-264).

Abnormal marker results usually reflect disease in patients with testicular cancer. False positive markers (e.g. hereditary AFP production) are rare but may result in significant overtreatment (chemotherapy, surgery). On the other hand, treatment monitoring by tumour markers is only possible in non-seminomatous germ cell tumours (NSGCT), while in seminoma patients treatment response has to be estimated by results of imaging methods (CT-scan, PET scan), which obviously have their limitations.

A search for new tumour markers for tumours of the reproductive system, especially testicular and ovarian cancers, specifically in the rather large marker-negative group reported above (⅓ of NSGCT and most seminomas) is therefore urgently needed.

It is an object of the present invention to provide novel strategies for diagnosis of tumours of the reproductive system, especially for ovarian and testicular tumours as well as for cervical cancer.

Therefore, the present invention provides a method for diagnosing tumours of the reproductive organs (i.e. the reproductive system) which method is characterised by determination of the afamin content in a sample of a body fluid or in a tissue sample, wherein a tumour is diagnosed if the afamin content in the sample is decreased compared to the afamin content in a sample from a person without a tumour of the reproductive organs.

Afamin is a 87 kDa protein belonging to the albumin group and having many things in common, structurally and in terms of biochemistry, with the proteins of this group, such as, e.g., with human serum albumin (HSA), human [alpha]-fetoprotein (AFP) or human vitamin D binding protein. Afamin has already been cloned and sequenced and thus is also available in recombinant form (WO 95/27059). Afamin is a glycoprotein primarily of hepatic origin that is secreted into the circulation. It has been shown that afamin occurs abundantly in plasma and other body fluids like follicular fluid, cerebrospinal and seminal fluid. Apart from its sequence homologies to albumin, little is known about the function of afamin. The possibility has been discussed that afamin has sterol binding sites, yet probably does not bind actin. Due to the existing, yet not overwhelming similarity between afamin and albumin, it is doubted that these proteins bind the same ligands (Lichenstein et al., The Journal of Biological Chemistry, 269 (27) (1994), pp. 18149-18154). It has also been shown in vitro and in vivo to possess vitamin E-binding properties (Voegele et al., 2002 Biochemistry 41:14532-14538). Mice in which the afamin gene was knocked out by targeted disruption, exhibited (among other phenotypes) testes with significantly reduced mean organ sizes and, in some cases, testicular cancer. Some female mice had grossly enlarged reproductive organs (uterus and ovar) suggesting tumours also in these organs. The use of afamin for determining the fertility of mammals has been described in WO 01/01148 A1.

For the present invention, the role for afamin in developing testicular cancer also in humans was investigated (in a case/control as well as in a monitoring design following curative treatment) in patients with tumours in the reproductive system. Afamin has surprisingly been identified as a remarkably significant tumour marker for these tumours. This was further demonstrated clinically with various forms of male germ cell tumours.

Preferably testicular or ovarian tumours are diagnosed according to the present invention. In particular, the present invention is specifically suited for germ cell tumours.

According to a preferred embodiment, the diagnosed tumour according to the present invention is selected from seminomas, non-seminomas, embryonal testicular tumour, teratoma, yolc sac or chorioncarcinoma, and mixtures of the above-mentioned tumours.

Preferred ovarian tumours to be diagnosed by the present method are selected from primary epithelial ovarian tumours, especially cystadenoma, cystadenomacarcinoma or Brenner tumour, primary mesenchymal ovarian tumours and mixed tumours, especially ovarian fibroma or adenofibroma, sex-cord tumours, especially granulosa cell tumour, theka cell tumour, androblastoma or gynandroblastoma, germ cell tumours, especially dysgerminoma, teratoma, dermoid, struma ovarii, embryonal carcinoma, polyembryoma, endodermal sinus tumour or malignant chorionepithelioma, or metastatically generated secondary ovarian tumours, especially from breast carcinoma, gastrointestinal carcinomas or corpus carcinoma, and mixtures of the above-mentioned tumours.

Preferred testicular (germ cell) tumours to be diagnosed according to the present invention are selected from germ cell derived testicular tumours, especially seminoma, orchioblastoma, teratocarcinoma, chorioncarcinoma or mixed tumours with partial seminoma, or non germ cell derived testicular tumours, especially tumours of the testicular stroma, Leydig cell tumour, Sertoli cell tumour or granulosa cell tumour, and mixtures of the above-mentioned tumours.

On the other hand, the method according to the present invention has also proven to be effective for the diagnosis of cervical cancer, especially already in early stages of this type of cancer (e.g. pre-stage 0, stage 0, I, IA or IB).

The present method can be combined with any other method for diagnosing tumours in the reproductive system, e.g. manual examination, histological examination or tumour marker diagnosis. It is particularly preferred to combine the present method with additional tests for other tumour markers or combinations of such markers, especially for tumours of the reproductive system, in the sample. Preferred additional markers for testicular tumours are alpha-fetoprotein, beta-subunit of human chorionic gonadotropin, lactate dehydrogenase, epidermal growth factor, NES-1 or i(12p)(Hellerstedt et al., 2002). Preferred additional markers for ovarian tumours are CA125, lysophosphatidylic acid (LPA), CA130 or alpha-folate receptor. A preferred additional marker for cervical tumor is SCC (squamous cell carcinoma antigen; Gadducci A et al., Biomed Pharmacother 2004, 58:24-38).

According to the present invention the afamin content of the sample is determined with a suitable afamin determination method and—due to a comparison with an afamin reference—analysed whether the afamin in the sample is decreased or not. This can be done e.g. by comparing the afamin content in the sample with an afamin standard, such an afamin reference value from a healthy individual or from an individual not having a tumour of the reproductive system. Alternatively (or in addition), a reference value from a patient with a tumour in the reproductive system is provided. The reference value may be provided e.g. in form of one or more reference samples, reference tables, reference curves or analogous means as well as combinations thereof. In analysing whether the amount in the sample is decreased, the skilled man in the art has a number of possibilities. For example, a direct comparison with published reference values of afamin in the body fluid or tissue. In any way, the method according to the present invention does not provide a final medical diagnosis, it provides an afamin value for one sample of unknown tumour status or from a person being at risk of or being suspected of having a tumour in the reproductive system compared to an afamin value of a given or virtual sample not having a tumour in the reproductive system, specifically a testicular tumour or an ovarian tumour. The final medical diagnosis is then given—independently from the in vitro diagnosing or analysation method according to the present invention—by the individual medically educated person entitled to such a diagnosis.

According to a preferred embodiment of the present invention, the afamin content in the sample is regarded as decreased, if it is at least 10% lower, preferably at least 30% lower, especially at least 50% lower, than the afamin content in a sample from a person without a tumour of the reproductive organs.

Alternatively, the afamin content in the sample is regarded as decreased according to the present invention, if it is at least 20% lower, preferably at least 40% lower, especially at least 60% lower, than the afamin content in a sample from a person without a tumour of the reproductive organs.

Preferably the person without a tumour of the reproductive organs is a healthy person with an afamin content of 50 to 70 mg, especially 60 mg, afamin per liter blood serum. The above mentioned % values are then calculated either from the 60 mg value or from the 50 mg lower limit (also depending on the comparative values for the specific body fluid (e.g. plasma or serum) or afamin-determination system).

The preferred body fluids or tissue samples are selected from blood, serum, plasma, cerebrospinal fluid, sperm fluid, follicular fluid, ovarium, testicle or epididymis.

Although all methods for determining afamin are suitable for the present invention, which allow distinguishing between a normal and a decreased afamin value, the afamin content is preferably determined with anti-afamin antibodies, especially monoclonal antibodies. Such antibodies may comprise a detection marker, preferably a chromogenic, fluorogenic or radioactive marker. According to a further aspect, the present invention relates to the use of a kit for determining the amount of afamin in a sample of a body fluid or in a tissue sample comprising afamin detection means and an afamin reference for diagnosing tumours of the reproductive organs. Kits for determination of afamin are well known in the art (e.g. WO 01/01148 or WO 95/27059). Preferably, the use according to the present invention is reduced to practice by applying a method according to the present invention as described above.

Among the usual components of such afamin determination kits, the afamin standard is specifically preferred (e.g. as a standard well in a microtiter ELISA or as standard dot or area on a genechip or protein (antibody) microarray chip.

The present invention is further described in the following examples and the drawing figures, yet without being restricted thereto.

Figure 1:
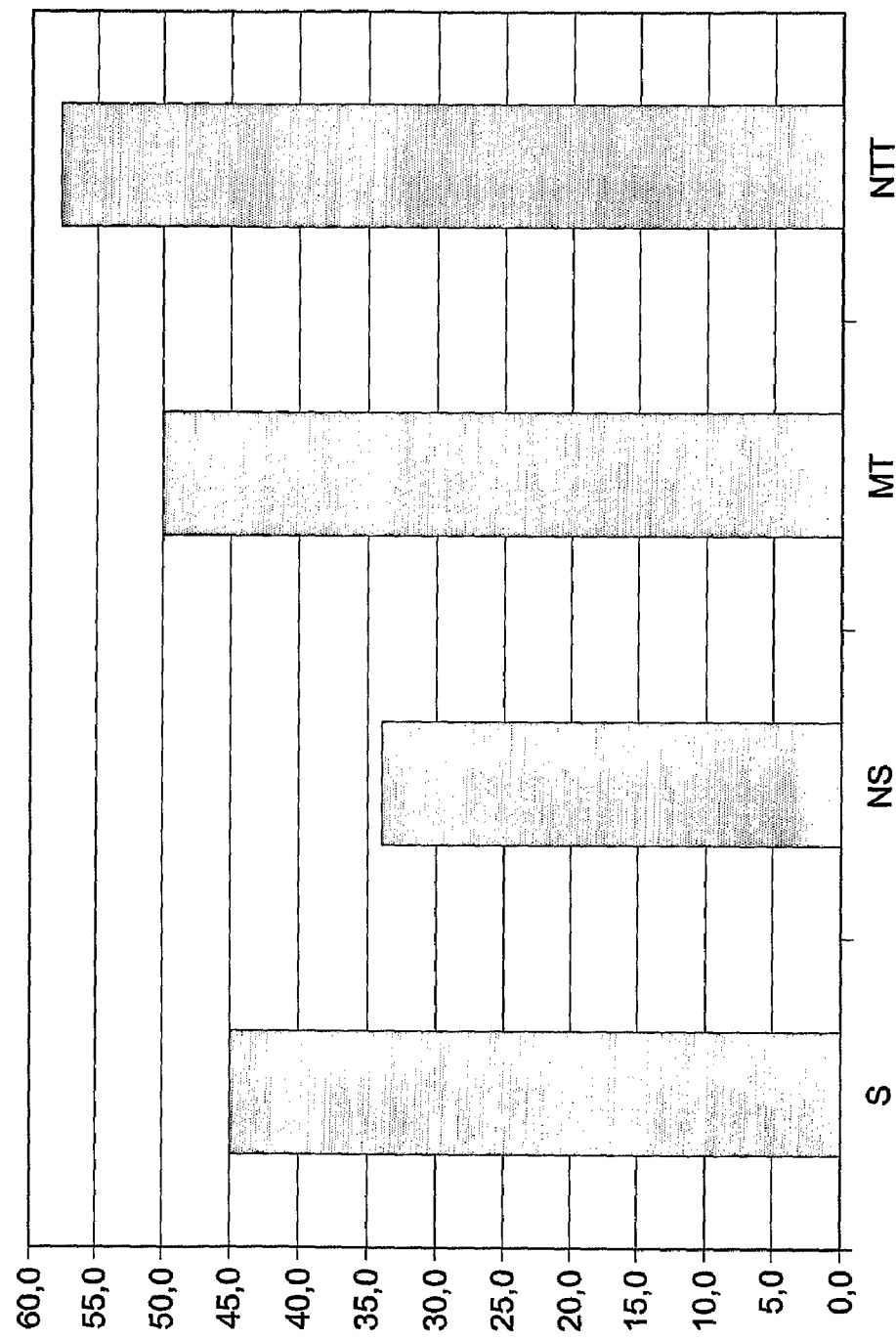
FIG. 1 shows the mean concentration of afamin [mg/l] in S=Seminom, NS=Nonseminom, MT=Mixed Tumour, NTT=NonTesticular Tumour.
Figure 2:
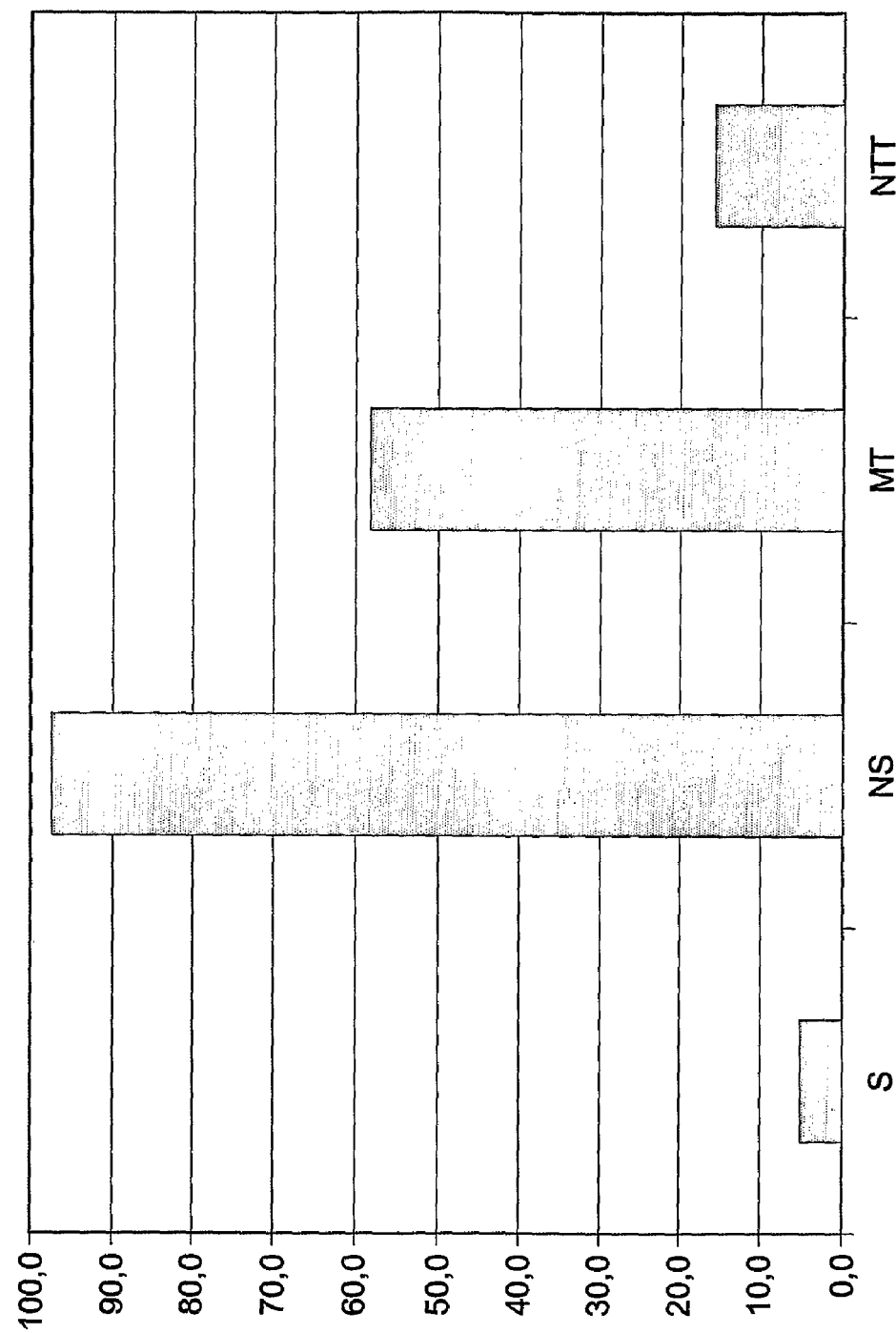
FIG. 2 shows the mean concentration of AFP [ng/ml] in S=Seminom, NS=Nonseminom, MT=Mixed Tumour, NTT=NonTesticular Tumour.
Figure 3:
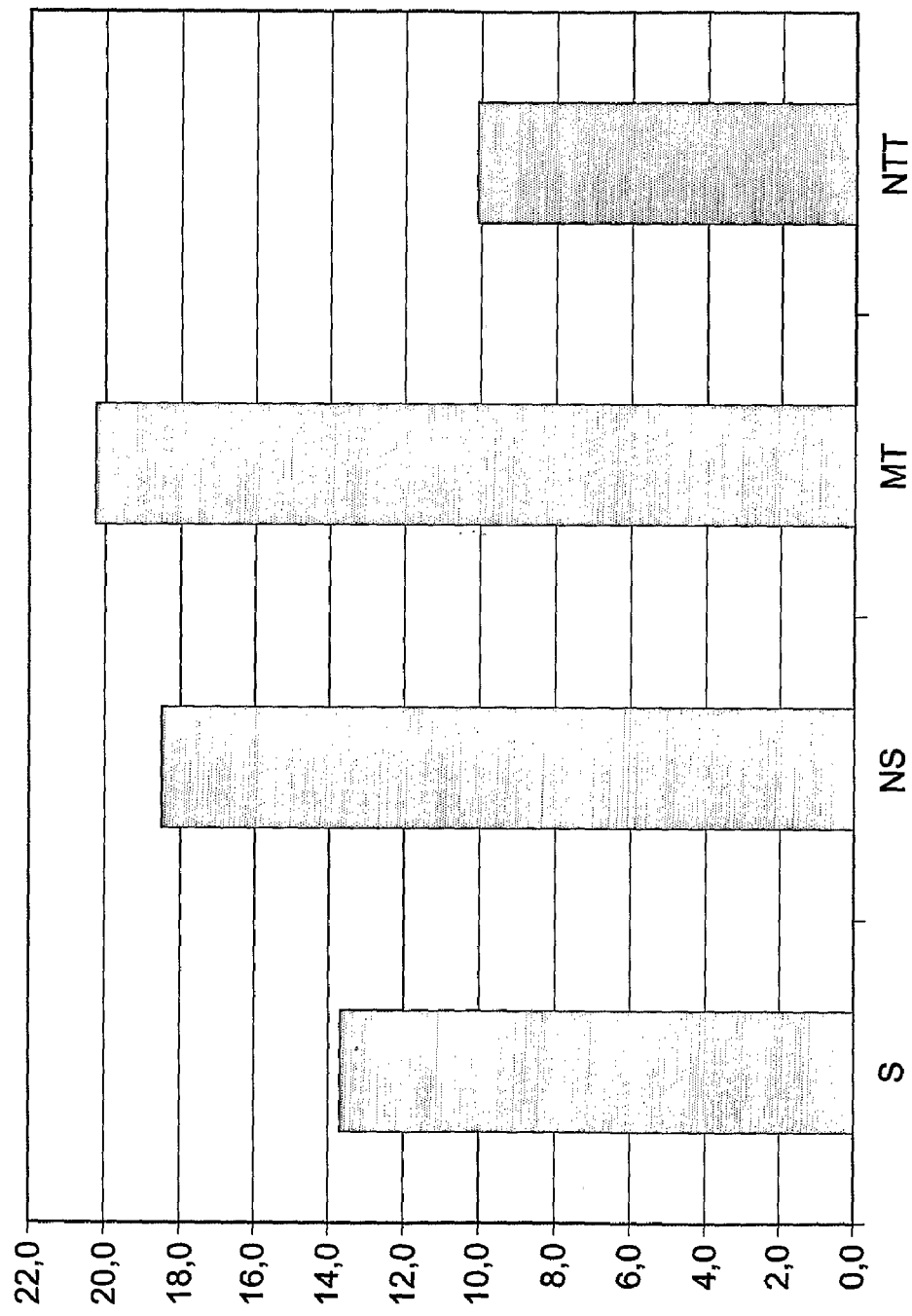
FIG. 3 shows the mean concentration of HCG [mIU/ml] in S=Seminom, NS=Nonseminom, MT=Mixed Tumour, NTT=NonTesticular Tumour.
Figure 4:
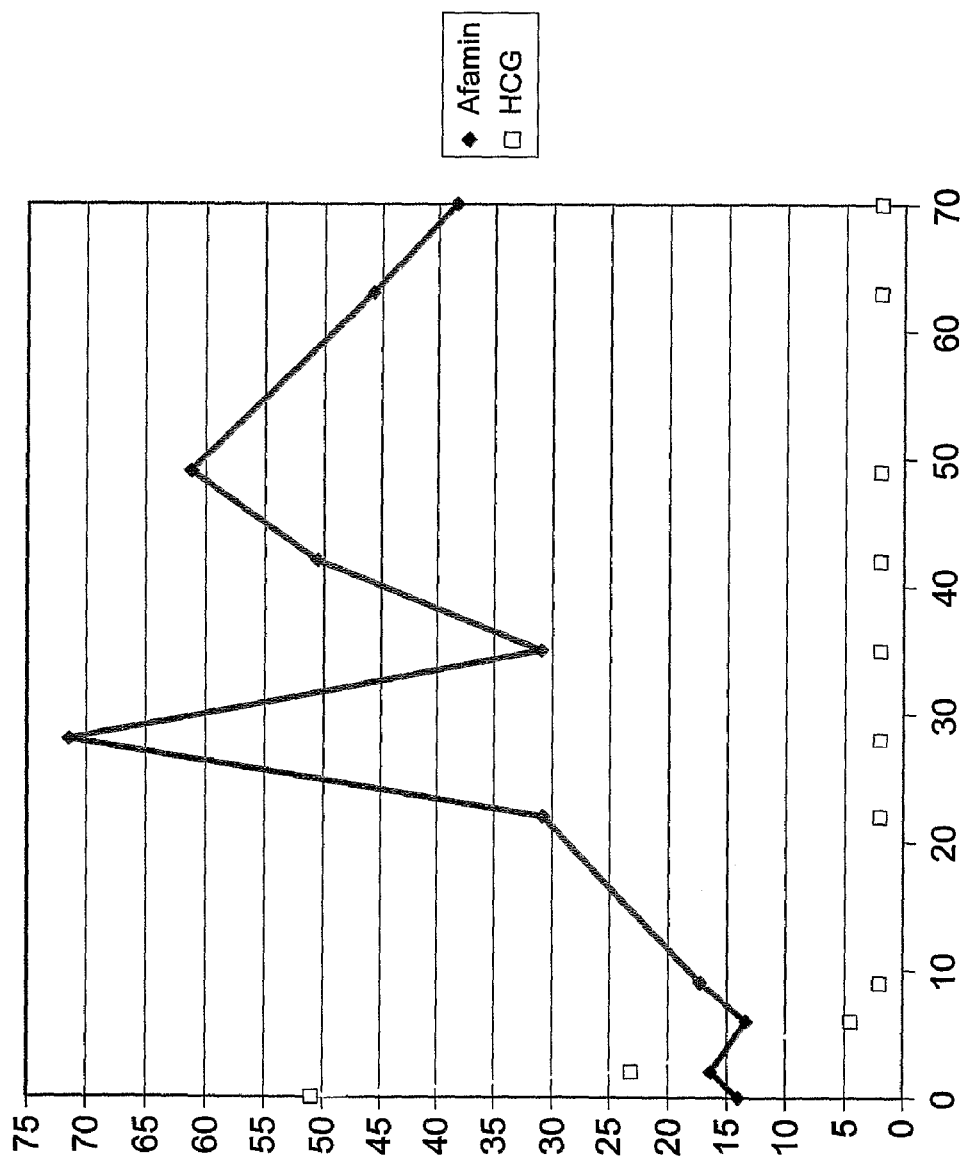

FIG. 4 shows the development of afamin serum concentration [mg/l] and HCG serum concentration [mIU/ml] during time (in days) of a representative patient with a seminome. Time point 0 indicates serum value from sample taken from the day prior tumour operation; other time points range up to 70 days postoperatively and show an increase of afamin values to normal values within the first 2 weeks after operation. Second curve shows respective values for serum HCG concentrations.

Figure 5:
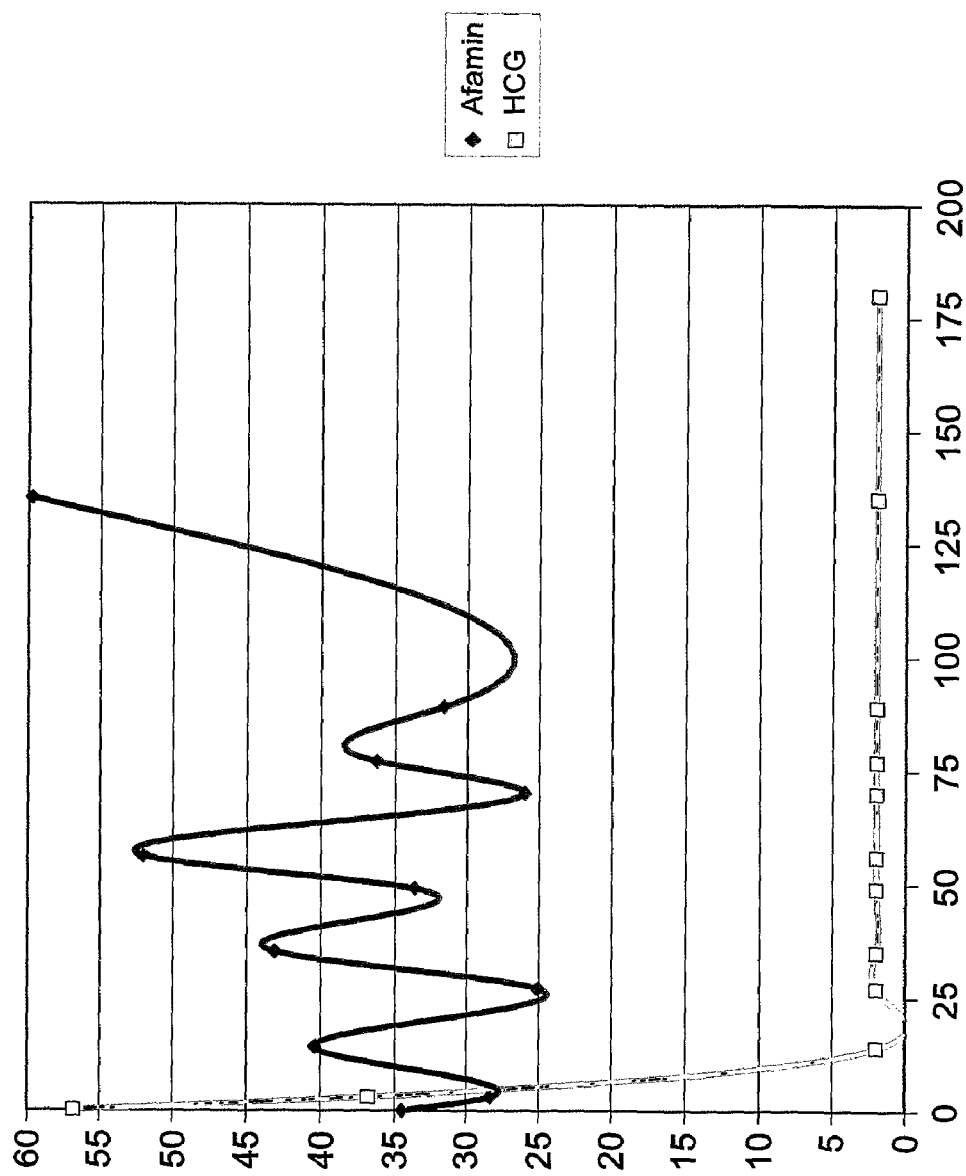

FIG. 5 shows the development of afamin serum concentration [mg/l] and HCG serum concentration [mIU/ml] during time (in days) of a representative patient with a seminome. Time point 0 indicates serum value from sample taken from the day prior tumour operation; other time points range up to 135 days postoperatively and show an increase of afamin values to normal values within the first 2 weeks after operation. Second curve shows respective values for serum HCG concentrations.

Figure 6:
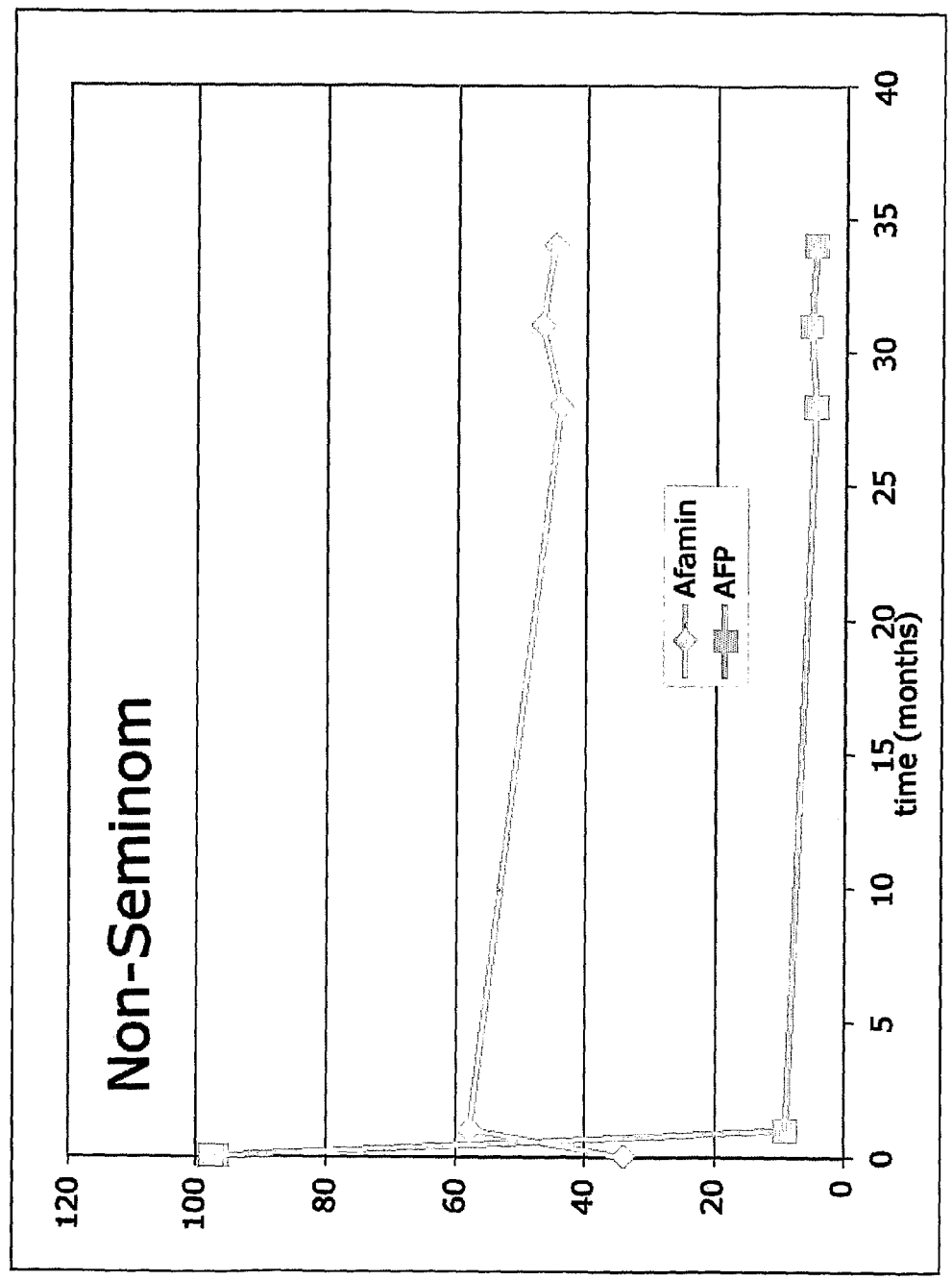

FIG. 6 shows the development of afamin serum concentration [mg/l] and AFP serum concentration [ng/ml] during time (in months) of a representative patient with a nonseminome. Time point 0 indicates serum value from sample taken from the day prior tumour operation; other time points range up to 34 months postoperatively and show an increase of afamin values to normal values within the first 2 weeks after operation. Second curve shows respective values for serum HCG concentrations.

Figure 7:
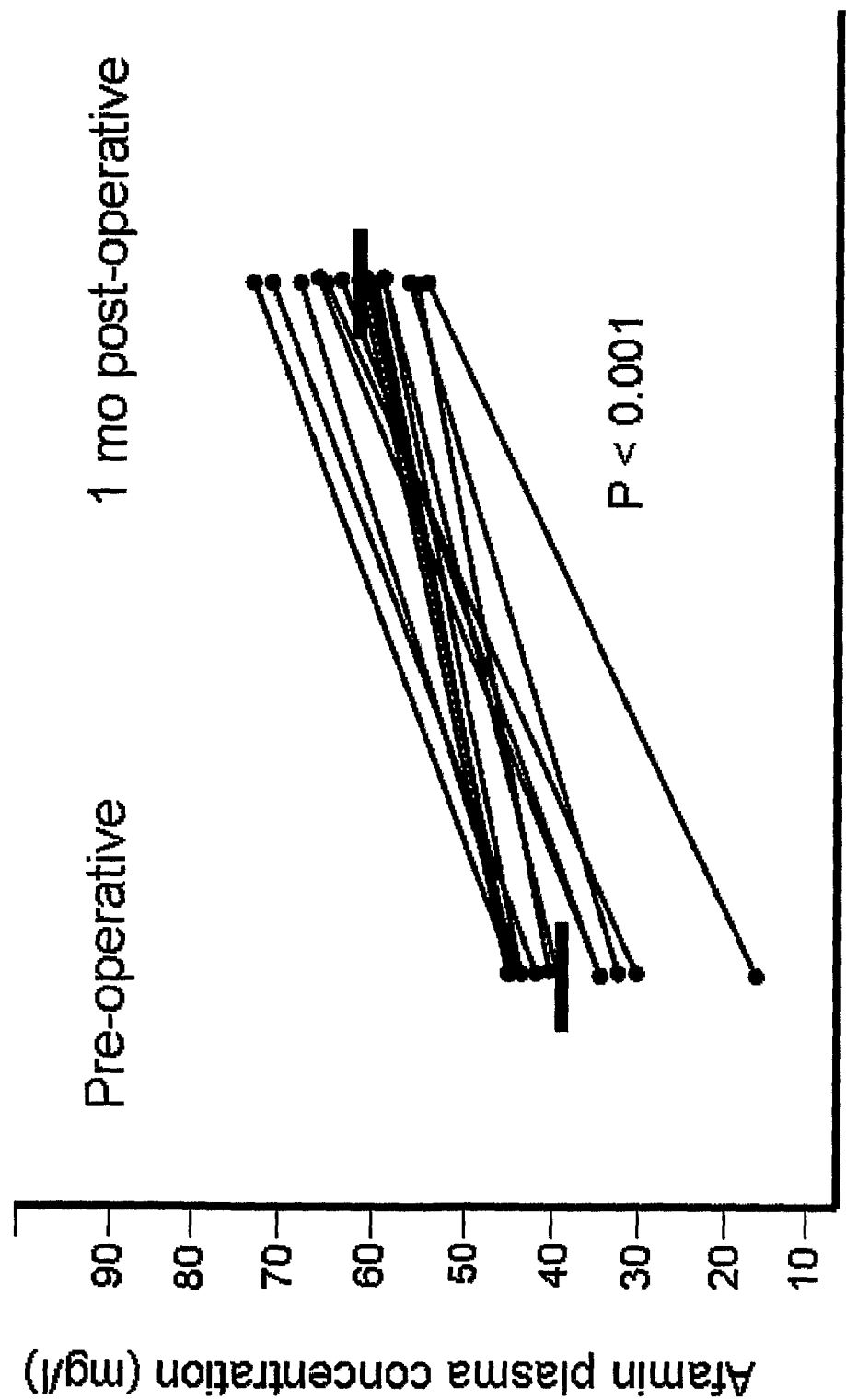

FIG. 7 shows that plasma concentrations of Afamin are significantly reduced in patients suffering from testicular cancer at the time of first cancer diagnosis and increase to physiological levels after successful surgical tumor/organ removal and increase to normal levels typically within one month (n=15).

Figure 8:
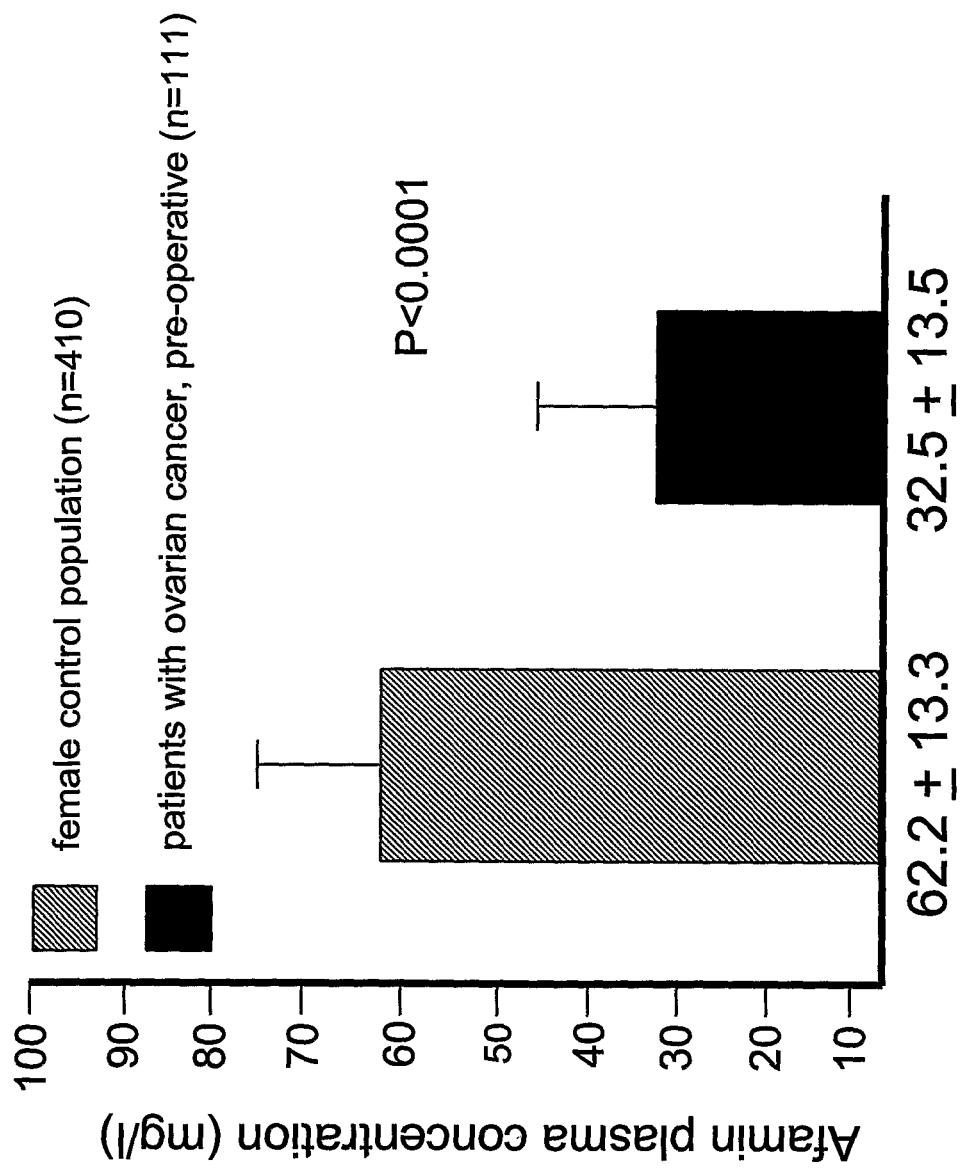

FIG. 8 shows plasma concentrations of Afamin (means ±standard deviation) of a population-based female control group (n=410, 95% CI 60.7-63.3) and patients with ovarian cancer (n=111, 95% CI 29.9-35.0) at the day of surgical tumor removal (preoperative).

Figure 9:
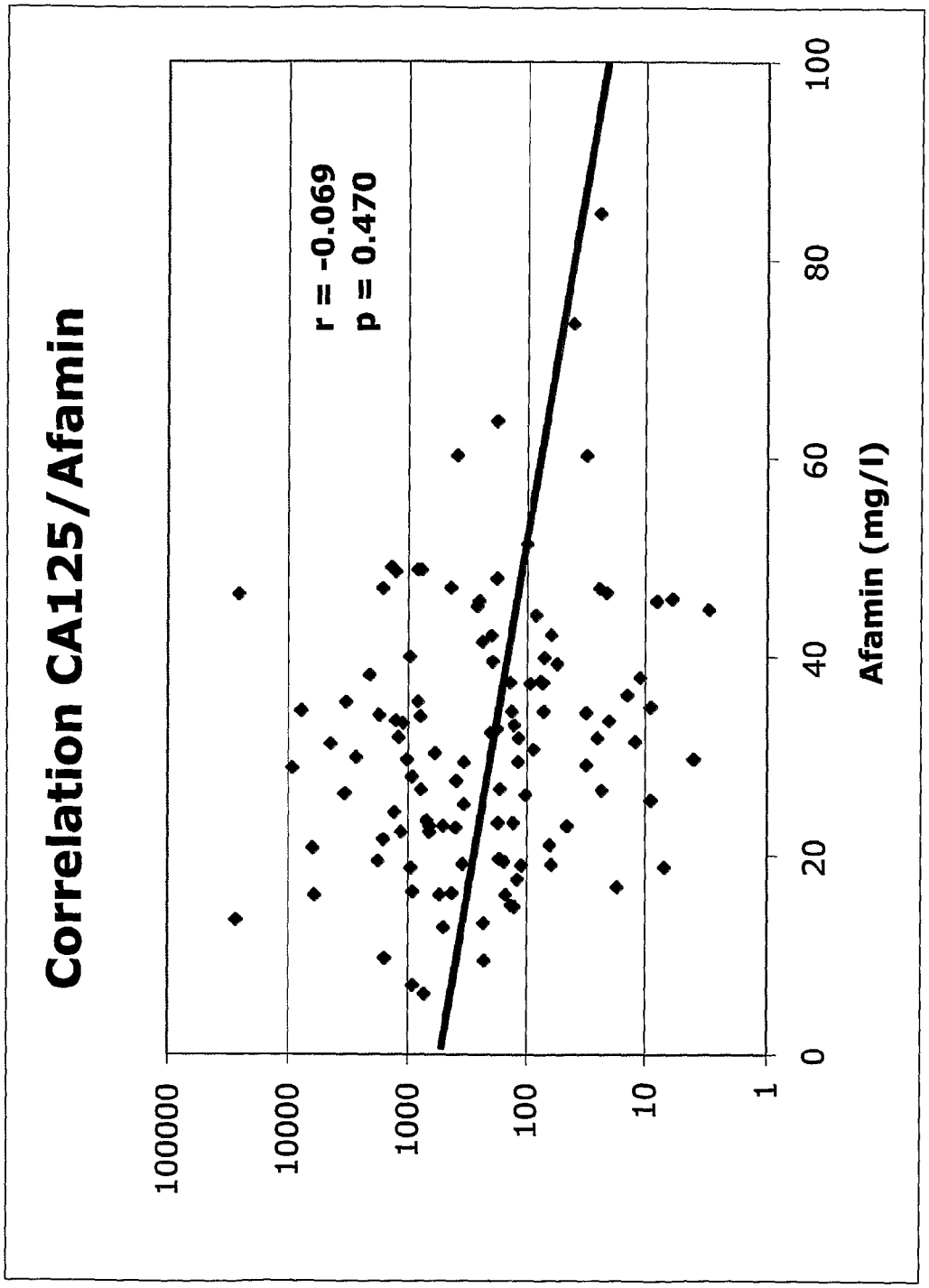

FIG. 9 shows correlation of plasma concentrations of Afamin and the conventional tumor marker CA125 in 111 patients with ovarian cancer at the day of surgical tumor removal (preoperative).

Figure 10:
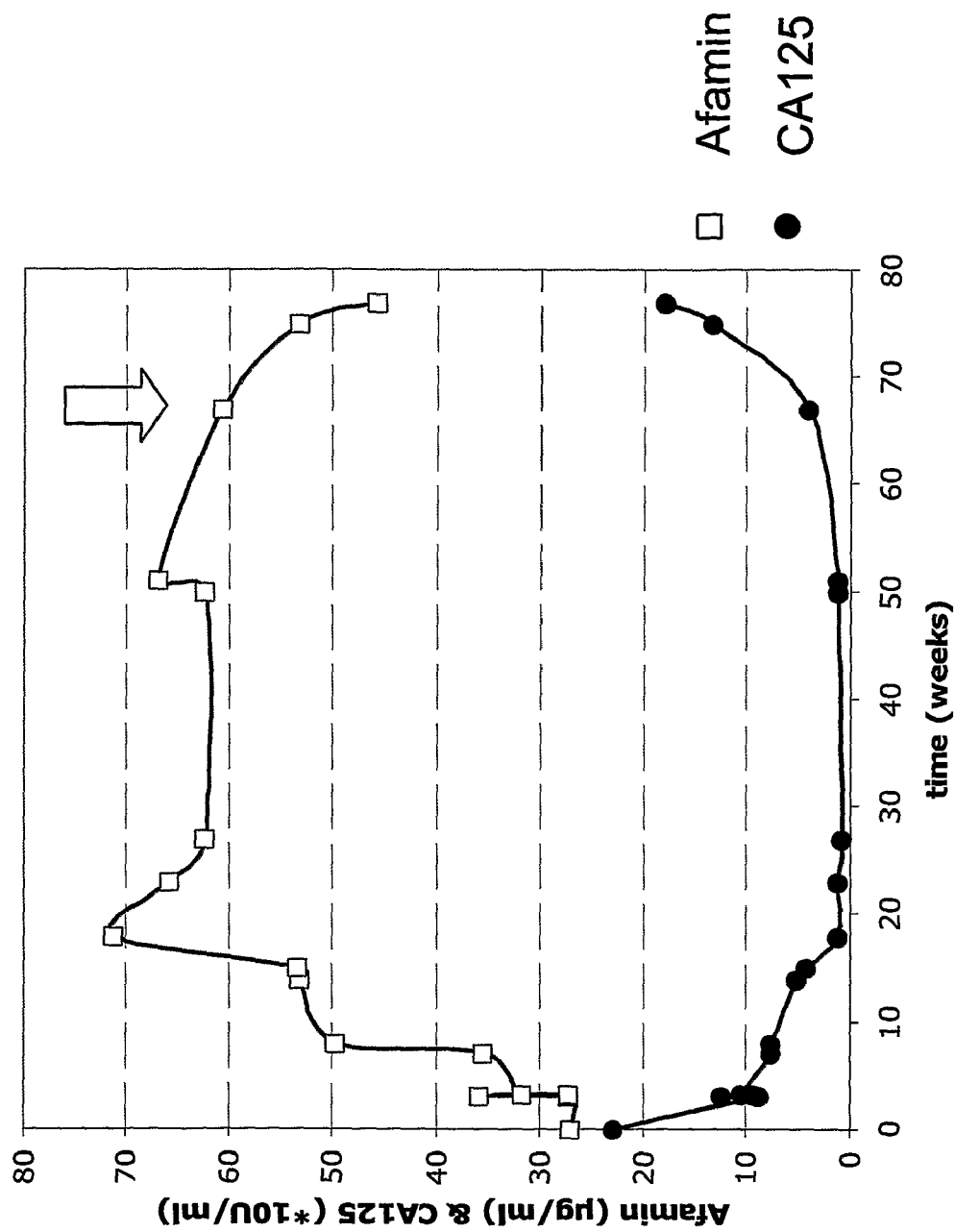

FIG. 10 shows plasma concentrations of Afamin and the conventional tumor marker CA125 of a representative patient with ovarian cancer at the day of surgical tumor removal (day 0) and about 80 weeks later at tumor recurrence. Reduced plasma concentrations of Afamin increase to normal levels of 60 µg/ml and decrease again in the case of tumor recurrence (indicated by the arrow)

Figure 11:
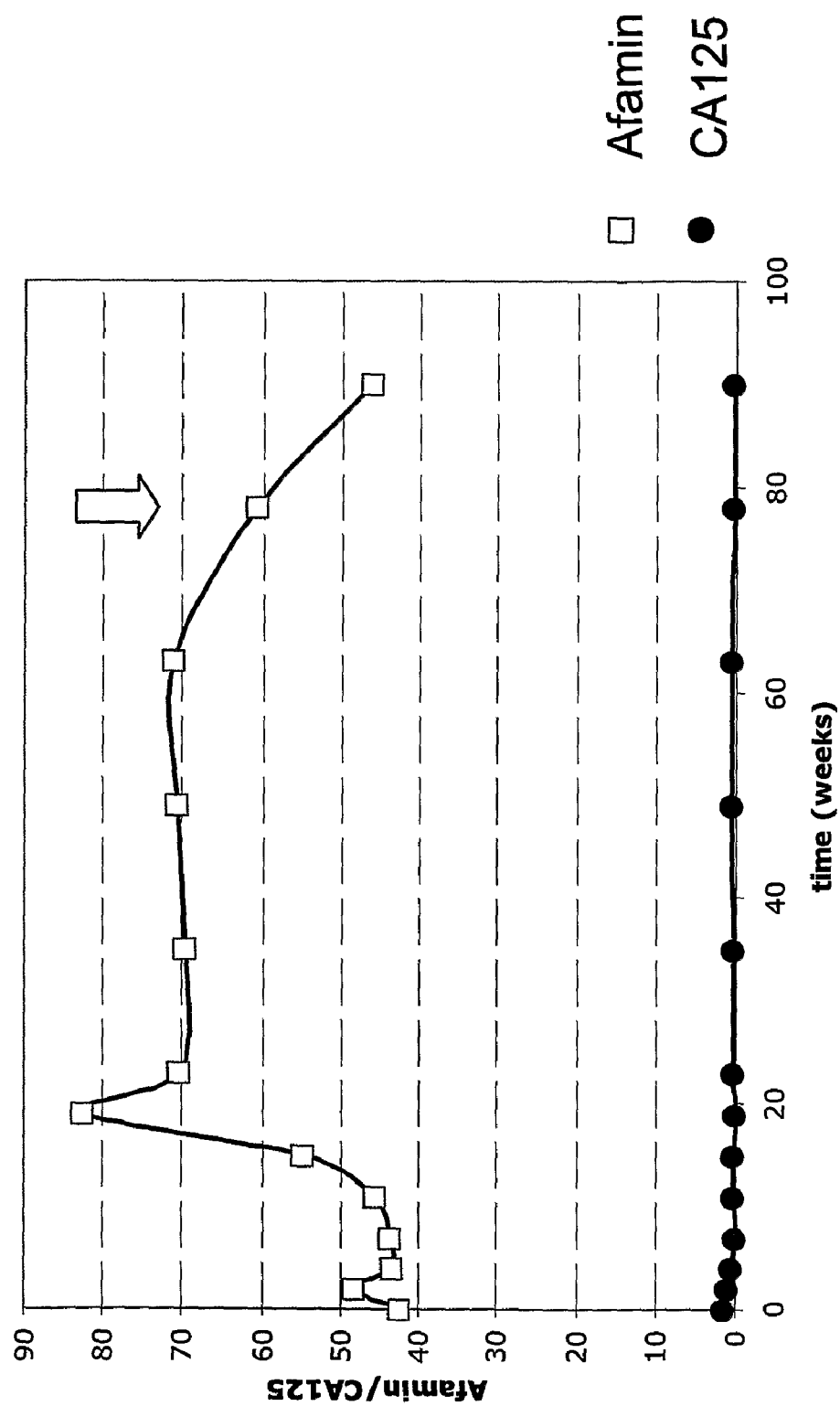

FIG. 11 shows plasma concentrations of Afamin and the conventional tumor marker CA125 of a representative patient with ovarian cancer at the day of surgical tumor removal (day 0) and about 80 weeks later at tumor recurrence. Reduced plasma concentrations of Afamin increase to normal levels of 60 µg/ml and decrease again in the case of tumor recurrence (indicated by the arrow). In comparison to CA125, Afamin is highly specific for gonadotrophic cancers.

Figure 12:
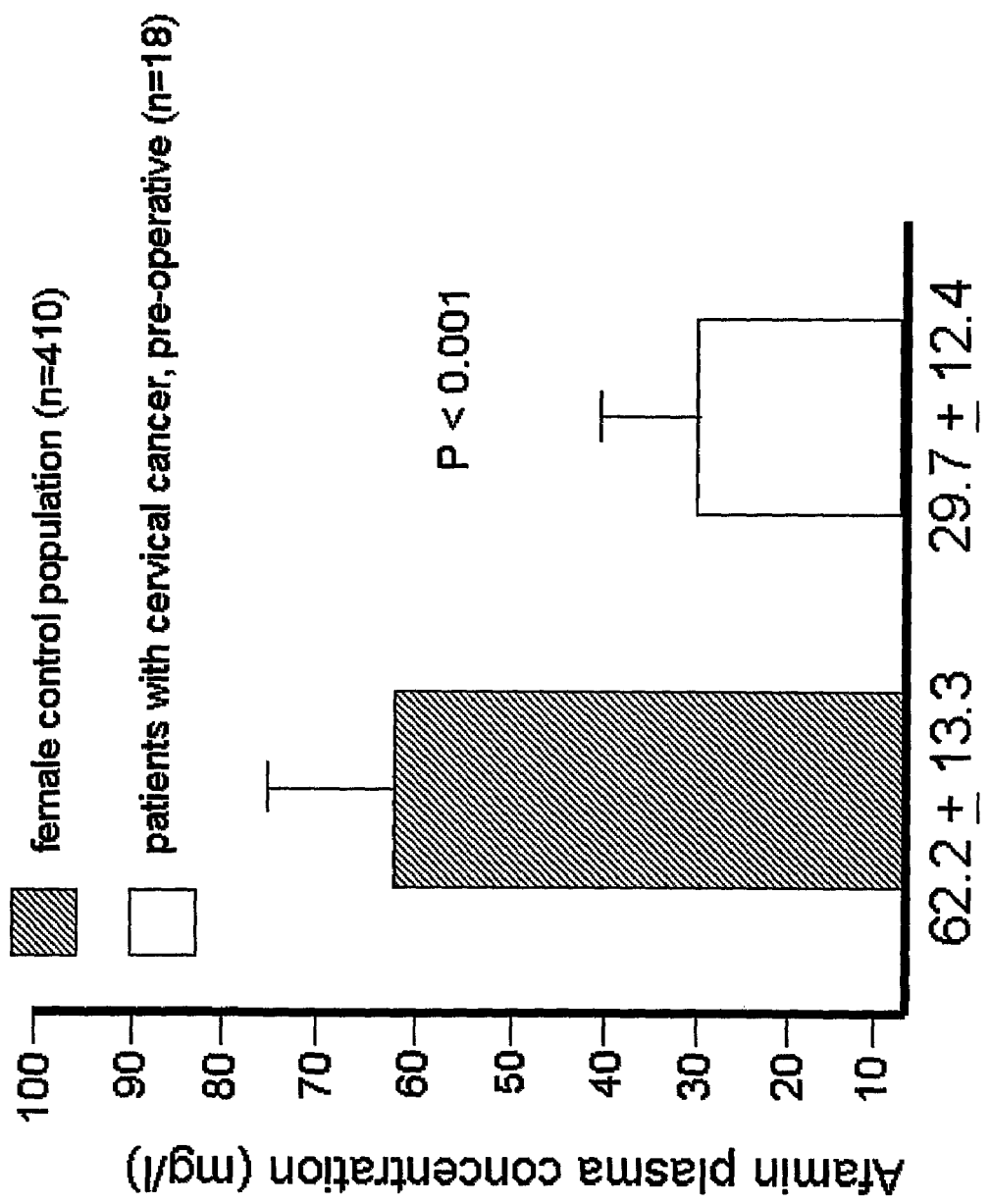

FIG. 12 shows plasma concentrations of Afamin (means ±standard deviation) of a population-based female control group (n=410) and patients with cervical cancer (n=18) at FIGO state IV at the day of surgical tumor removal (preoperative).

Figure 13:
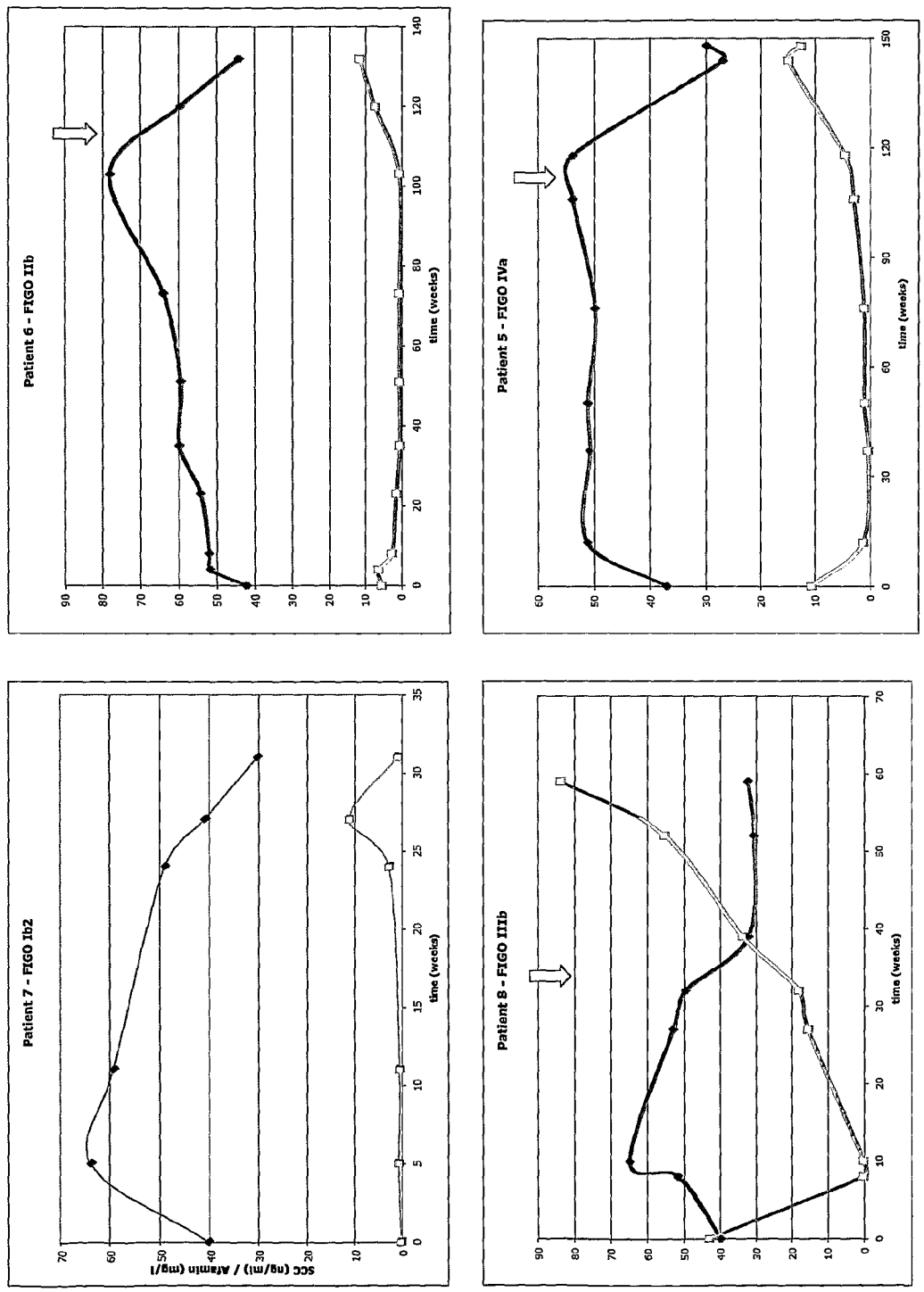

FIG. 13 shows plasma concentrations of Afamin (diamonds) and the conventional tumor marker SCC (squares) of 4 representative patients with cervical cancer at FIGO stages I-IV at the day of surgical tumor removal (day 0, preoperative) and after varying times of observation until tumor recurrence (arrow). Reduced plasma concentrations of Afamin increase to normal levels and decrease again in the case of tumor recurrence.

EXAMPLES

Patients and Methodology

From January 2004 to January 2005, 16 testicular cancer patients (seminoma, n=11, NSCGT, n=1, mixed tumours, n=4) were diagnosed and treated at the department of Urology. Testicular tumours were classified based on histology after inguinal orchiectomy. 4 patients were false-positively diagnosed on the basis of elevated AFP or HCG levels, 2 of them were histologically diagnosed having bladder cancer.

Immunometric HCG and AFP analyses of serum were conducted using the ADVIA® Centaur Immunoassay System (Bayer Diagnostics, Germany) with direct chemiluminescence technology. A value >10 ng/ml and >10 mIU/ml was considered pathological for AFP and hCG, respectively. Total protein was measured with a colorimetric assay (Folin-Cieu-Calteau, Merck-Chemicals, Darmstadt, Germany).

Serum concentrations of afamin were determined by a recently described sandwich ELISA (Voegele et al., 2002) using an affinity-purified polyclonal anti-human afamin rabbit antibody for coating microtiter plates and the POX-conjugated monoclonal anti-human mouse antibody N13 for detection. Afamin that was purified from human plasma and quantified by amino acid compositional analysis served to calibrate a secondary plasma sample.

AFP and HCG were analysed at the time of diagnosis and prior orchiectomy, frequently (at least bi-weekly) during subsequent therapy (chemotherapy, retroperitoneal surgery) and at least three monthly in follow-up. Afamin was measured from frozen samples at the end of the study period.

Results

Afamin was significantly decreased in patients with all 3 investigated forms of testicular cancer when compared to a random population-based control group (Table 1, detailed data in tables 2 and 3 and in the figures). Values increased to normal levels within a few weeks very much comparable to the normalisation of HCG/AFP levels. Total protein plasma levels were normal in patients and did not change during treatment and observation.

Most interestingly, normal afamin levels were found in 4 patients who had either elevated HCG or AFP levels but showed no signs of testicular tumour by histological examination. Two of them, however, were diagnosed positively for bladder cancer.

TABLE 1

| Histology | AFP | HCG | Afamin |
|---|---|---|---|
| Seminoma | normal | elevated | decreased |
| Non-Seminoma | elevated | elevated | decreased |
| Mixed tumor | elevated | elevated | decreased |
| No testicular tumor | elevated | elevated | normal |

Discussion

The present results are the first report of a new tumour marker from human plasma that identifies testicular tumour independent of its subtype (S, NS, MT) by significantly decreased plasma levels and an increase to normal values after surgical removal of tumour. In the present small study group it thus provides, in contrast to routinely used tumour markers, a reliable marker for all groups of cancer.

Four patients have been detected by reduced afamin levels that do not show abnormalities of the routinely used parameters (thus reducing false negatives). Four cases were discovered in whom afamin levels were normal, HCG and/or AFP values were elevated. These findings helped to reduce false positive and negative results due to unspecificities of those classical markers.

Taken together, diagnosing afamin in testicular patients, as a representative form of tumours of the reproductive system, increases the detection specificity compared to specific markers known and applied in the art. The second important issue is the general applicability of decreased afamin values for all forms of testicular cancer. The present longitudinal observation of normalisation of values after curative treatment strongly confirms the significance of afamin as a valuable tumour marker for testicular cancer.

Pathological factors, expressed in the testicular tumour might suppress afamin production and secretion in the liver. Alternatively, the growing tumour might increasingly deprive plasma from ligands which are carried by afamin. Vitamin E which is the so far only known physiological ligand of afamin (Voegele et al., 2002 Biochemistry 41:14532-14538) has been assigned several roles in carcogenesis (Sigounas et al., 1997 Nutr Cancer 28:30-35).

TABLE 2

| ID | AFA S | AFA NS | AFA MT | AFA NTT | AFA CG | AFP S | AFP NS | AFP MT | AFP NTT | HCG S | HCG NS | HCG MT | HCG NTT |
|---|---|---|---|---|---|---|---|---|---|---|---|---|---|
| 1 | 32 | | | | | 6.7 | | | | 2 | | | |
| 2 | 51 | | | | | 12.7 | | | | 2 | | | |
| 3 | 63 | | | | | 1.3 | | | | 2 | | | |
| 4 | | | | 52 | | | | | 34.7 | | | | 2 |
| 5 | | | | 58 | | | | | 3.7 | | | | 34.4 |
| 6 | | 34 | | | | | 97.5 | | | | 18.5 | | |
| 7 | 34 | | | | | 3.3 | | | | 2 | | | |
| 8 | | | 39 | | | | | 98.3 | | | | 33.7 | |
| 9 | | | 54 | | | | | 32.3 | | | | 17.6 | |
| 10 | 83 | | | | | 3.6 | | | | 2 | | | |
| 11 | 30 | | | | | 3.4 | | | | 56.8 | | | |
| 12 | | | | 69 | | | | 12.9 | | | | | 2 |
| 13 | 14 | | | | | 6.9 | | | | | 51 | | |
| 14 | | | | 52 | | | | | 11.6 | | | | 2 |
| 15 | | | 63 | | | | | 44.1 | | | | 9.5 | |
| 16 | 49 | | | | | 2.8 | | | | | 27.7 | | |
| 17 | 50 | | | | | 3.3 | | | | 2 | | | |
| 18 | 43 | | | | | 4.3 | | | | 2 | | | |
| 19 | 46 | | | | | 8.6 | | | | 1.1 | | | |
| 20 | | | 44 | | | | | 3.1 | | | | 27.8 | |
| mean | 45.0 | 34.0 | 50.0 | 57.8 | 62.6 | 5.2 | 97.5 | 58.2 | 15.7 | 13.7 | 18.5 | 20.3 | 10.1 |
| SD | 18.2 | 0 | 10.7 | 8.1 | 15.1 | | | | | | | | |
| | 2 × false neg, 8 × decr, 1 × incr (S) | | | | | 10 × false neg, 1 × incr (S) | | | | 8 × false neg, 3 × false neg | | | |
| | 1 × decr (NS) | | | | | 1 × incr (NS) | | | | 1 × incr (NS) | | | |
| | 2 × false neg, 1 × decr (MT) | | | | | 3 × incr, 1 × normal (MT) | | | | 3 × incr (MT) | | | |
| | 4 × normal (NTT) | | | | | 3 × false pos (NTT) | | | | 3 × false neg, 1 × incr (NTT) | | | |

Significance Afamin between Seminom und control group: p = 0.003
Significance Afamin between Nonseminom and control group: p = 0.000
Normal Afa Range 50-70 mg/l
AF: >10 ng/ml × pathological
HCG: >10 mIU/ml × pathological
AFA = Afamin,
AFP = Alphafetoprotein,
HCG = human chorionic gonadotropin
S = Seminom,
NS = Nonseminom,
MT = Mixed Tumor,
NTT = NonTesticular Tumor
CG = control group, population-based, n = 360

TABLE 3

| Zeit | Afamin | HCG | AFP | Zeit | Afamin | AFP | HCG | Afamin | Zeit | Afamin | AFP |
|---|---|---|---|---|---|---|---|---|---|---|---|
| 0 | 14 | 51 | 6.9 | 0 | 34.5 | 3.4 | 56.8 | 34.5 | 0 | 34.00 | 97.5 |
| 2 | 16.38 | 23.2 | 5.3 | 3 | 28.34 | 2.1 | 36.8 | 28.34 | 1 | 58.00 | 9 |
| 6 | 13.35 | 4.5 | 3.5 | 14 | 40.39 | 4.2 | 2 | 40.39 | 28 | 44.00 | 4.6 |
| 9 | 17.28 | 2 | 3.5 | 27 | 25.06 | 5.6 | 2 | 25.06 | 31 | 47.00 | 5.5 |
| 22 | 30.82 | 2 | 4.1 | 35 | 43.15 | 5.6 | 2 | 43.15 | 34 | 45.00 | 4.6 |
| 28 | 71.45 | 2 | 12.9 | 49 | 33.64 | 4.4 | 2 | 33.64 | | | |
| 35 | 30.95 | 2 | 5.8 | 56 | 52.03 | 8.2 | 2 | 52.03 | | | |
| 42 | 50.53 | 2 | 8.6 | 70 | 25.98 | 4.8 | 2 | 25.98 | | | |
| 49 | 61.19 | 2 | 10.8 | 77 | 36.24 | 8.8 | 2 | 36.24 | | | |
| 63 | 45.74 | 2 | 5.4 | 89 | 31.61 | 12.4 | 2 | 31.61 | | | |
| 70 | 38.37 | 2 | 7.4 | 135 | 59.77 | 6.1 | 2 | 59.77 | | | |
| | | | | 180 | | 4.6 | 2 | | | | |

Further Clinical Investigations:

Testicular Cancer:

In order to establish afamin as tumor marker also for monitoring the disease development (disappearance and recurrence of tumor) and thus confirm the results from the pilot study shown in FIGS. 1-3, 15 patients with diagnosed testicular cancer were measured prior surgical tumor removal and approximately 1 month thereafter. Decreased afamin plasma levels returned to values typical for the healthy population (see Table 2). Afamin values stay within normal range even after prolonged observation (up to several years) indicating no tumor recurrence. This is in agreement with the clinical experience of very rare testicular tumor recurrence.

Ovarian Cancer:

Based on analogy and on preliminary findings of suggested tumors in reproductive organs in afamin-knock-out female mice Afamin levels were also investigated in human patients with ovarian cancer. The diagnostic situation is similarly unsatisfactory in this disease as well since the conventionally used tumor marker CA125 is very unspecific for ovarian cancer and therefore only suitable for tumor monitoring.

Similar to patients with testicular cancer, significantly reduced plasma concentrations of afamin were found in 111 patients with ovarian cancer when compared to population-based and age-matched controls (n=410). The difference was even more pronounced (32 vs. 62 mg/l; FIG. 8) as in testicular cancer patients.

When afamin and CA 125 plasma concentrations were correlated with each other, a very weak, non-significant negative correlation was observed (FIG. 9). This indicates virtually no association between these 2 markers.

In order to confirm the suitability of afamin as ovarian cancer tumor marker also in the monitoring design 10 patients were investigated longitudinally from the preoperative day at cancer diagnosis until tumor recurrence. Significantly decreased afamin values at time of diagnosis increased to values of healthy controls (a representative investigation is seen in FIG. 10). In some cases, reduced afamin concentrations at tumor diagnosis were observed also in the absence of increased CA125 markers (FIG. 11) indicating a higher tumor specificity of afamin as compared with CA125.

Cervical Cancer:

Finally, also a group of patients with another tumor of reproductive organs, cervical cancer which is the 2nd most frequent cancer in females was investigated. No specific serum tumor marker exists at all for the identification of this frequent cancer. The conventionally used plasma marker SCC (Squamous cell carcinoma antigen) is again not specific enough for cervical cancer.

By the present invention not only significantly reduced plasma concentrations of afamin in 18 patients with cervical cancer could be shown, but again the suitability of afamin as monitoring tumor marker in the longitudial design (n=16) could be demonstrated. Afamin was decreased in all investigated FIGO stages of the cancer, increased to normal values of healthy controls after tumor removal and decreased again at tumor recurrence (FIGS. 12 and 13).

The invention claimed is:

1. A method for diagnosing testicular cancer, wherein the testicular cancer is a seminoma, a non-seminoma, or a mixed cancer of seminoma and non-seminoma, comprising determining a decrease in of the afamin content in a blood, serum, or plasma sample, wherein the testicular cancer is diagnosed if the afamin content in the sample is decreased compared to an afamin content normally present in blood, serum or plasma of a person without the testicular cancer.

2. The method of claim 1, comprising comparing the afamin content in the sample with an afamin standard.

3. The method of claim 2, wherein the afamin standard is an afamin reference value of 50 mg to 70 mg of afamin per liter of blood serum of an individual not having the testicular cancer.

4. The method of claim 1, wherein the testicular cancer is seminoma.

5. The method of claim 1, wherein at least one additional marker for cancer is determined in the sample.

6. The method of claim 5, wherein the at least one additional marker is alpha-fetoprotein, beta-subunit of human chorionic gonadotropin, lactate dehydrogenase, epidermal growth factor, NES-1, or i(12p).

7. The method of claim 1, wherein testicular cancer is diagnosed if the afamin content in the sample is at least 10% lower than an afamin content in a person without a testicular cancer.

8. The method of claim 7, wherein testicular cancer is diagnosed if the afamin content in the sample is at least 20% lower than an afamin content in a person without testicular cancer.

9. The method of claim 8, wherein testicular cancer is diagnosed if the afamin content in the sample is at least at least 30% lower than an afamin content in a person without testicular cancer.

10. The method of claim 9, wherein testicular cancer is diagnosed if the afamin content in the sample is at least 40% lower than an afamin content in a person without testicular cancer.

11. The method of claim 10, wherein testicular cancer is diagnosed if the afamin content in the sample is at least 50% lower than an afamin content in a person without testicular cancer.

12. The method of claim 11, wherein testicular cancer is diagnosed if the afamin content in the sample is at least 60% lower than an afamin content in a person without testicular cancer.

13. The method of claim 1, wherein the afamin content normally present in a sample from a person without a testicular cancer is further defined as 50 to 70 mg afamin per liter blood serum.

14. The method of claim 13, wherein the afamin content normally present in a sample from a person without a testicular cancer is further defined as 60 mg afamin per liter blood serum.

15. The method of claim 1, wherein the sample is serum.

16. The method of claim 1, wherein the afamin content is determined with an anti-afamin antibody.

17. The method of claim 16, wherein the anti-afamin antibody is a monoclonal antibody.

18. The method of claim 16, wherein the antibody comprises a detection marker.

19. The method of claim 18, wherein the detection marker is a chromogenic, fluorogenic or radioactive marker.

20. The method of claim 1, further defined as comprising using a kit for determining the amount of afamin in a blood, serum, or plasma sample comprising afamin detection means and an afamin reference for diagnosing testicular cancers.

21. The method of claim 20, wherein the kit contains a standardized amount of afamin.

* * * * *

UNITED STATES PATENT AND TRADEMARK OFFICE
CERTIFICATE OF CORRECTION

PATENT NO. : 7,767,406 B2 Page 1 of 1
APPLICATION NO. : 11/814905
DATED : August 3, 2010
INVENTOR(S) : Hans Dieplinger It is certified that error appears in the above-identified patent and that said Letters Patent is hereby corrected as shown below:

In claim 1, column 13, line 42, delete "in of the" and insert --in the-- therefor.

In claim 9, column 14, lines 16-17, delete "at least at least" and insert --at least-- therefor.

Signed and Sealed this

Twenty-sixth Day of October, 2010

David J. Kappos
*Director of the United States Patent and Trademark Office*